(12) United States Patent
Jones

(10) Patent No.: US 11,324,964 B2
(45) Date of Patent: May 10, 2022

(54) APPARATUS FOR DERMATOLOGICAL TREATMENT

(71) Applicant: iPulse Limited, Swansea (GB)

(72) Inventor: Stuart Terry Jones, Swansea (GB)

(73) Assignee: IPULSE LIMITED, Swansea (GB)

( * ) Notice: Subject to any disclaimer, the term of this patent is extended or adjusted under 35 U.S.C. 154(b) by 472 days.

(21) Appl. No.: 16/332,742

(22) PCT Filed: Sep. 12, 2017

(86) PCT No.: PCT/GB2017/052674
§ 371 (c)(1),
(2) Date: Mar. 12, 2019

(87) PCT Pub. No.: WO2018/046967
PCT Pub. Date: Mar. 15, 2018

(65) Prior Publication Data
US 2021/0283422 A1    Sep. 16, 2021

(30) Foreign Application Priority Data

Sep. 12, 2016   (GB) .................................... 1615448

(51) Int. Cl.
*A61N 5/06* (2006.01)
*A61N 5/00* (2006.01)

(52) U.S. Cl.
CPC ...... *A61N 5/0617* (2013.01); *A61N 2005/005* (2013.01); *A61N 2005/0632* (2013.01);
(Continued)

(58) Field of Classification Search
CPC ............ A61N 5/0617; A61N 2005/005; A61N 2005/0632; A61N 2005/0644; A61N 2005/0654
See application file for complete search history.

(56) References Cited

U.S. PATENT DOCUMENTS 8,475,507 B2 *  7/2013  Dewey ................. A61N 5/0616
                                                  607/89
2009/0306636 A1  12/2009  Ben-Israel et al.
(Continued)

FOREIGN PATENT DOCUMENTS

JP       200922333 A    2/2009
WO          0030714 A1   6/2000
WO       2014199365 A1  12/2014

OTHER PUBLICATIONS

Search Report issued in GB Application No. 1615448.6 dated Feb. 9, 2017.
(Continued)

*Primary Examiner* — Jonathan T Kuo
(74) *Attorney, Agent, or Firm* — Troutman Pepper Hamilton Sanders LLP; Ryan A. Schneider

(57) ABSTRACT

The present invention relates to a light emitting device for providing dermatological treatment. The present invention comprises a housing structure for housing a light emitting source, a fan and a duct. The light emitting source is arranged to emit light energy to external of the device and the fan is configured for directing air heated by operation of the light emitting source into the duct. The duct is arranged to direct heated air in an airstream pathway from an outlet port of a distal end of the duct and through an aperture in the housing structure where the housing structure and the duct are relatively arranged such that no part of the housing structure extends into the air stream pathway in order to minimise heat exchange from the heated air to the housing structure.

22 Claims, 3 Drawing Sheets

(52) U.S. Cl.
CPC ............... *A61N 2005/0644* (2013.01); *A61N 2005/0654* (2013.01)

(56) References Cited

U.S. PATENT DOCUMENTS

| | | | | |
|---|---|---|---|---|
| 2012/0165682 A1* | 6/2012 | Keeney | ............... | A61B 5/0059 600/476 |
| 2012/0197357 A1* | 8/2012 | Dewey | ............... | A61N 5/0616 607/89 |
| 2013/0060309 A1* | 3/2013 | Bradley | ............... | A61N 5/0616 607/100 |

OTHER PUBLICATIONS

International Search Report and Written Opinion issued in International Application No. PCT/GB2017/052674 dated Dec. 19, 2017.

\* cited by examiner

APPARATUS FOR DERMATOLOGICAL TREATMENT

The present invention relates to a light emitting device for providing dermatological treatment.

The use of light is widely known for use in various treatments of tissue for both therapeutic and cosmetic purposes, including but not limited to hair removal, treatment of acne and lesions and tissue rejuvenation.

A typical light emitting device for dermatological treatment comprises a charge storage device in the form of a capacitor, a housing, a light emitting source in the form of a flashlamp and a cooling fan and a housing arrangement.

In operation energy is released from the capacitor through the flashlamp thereby generating an intense pulse of light energy. Generation of the intense pulse of light energy by the flashlamp has the unwanted side effect of generating a significant amount of heat. In order to prevent overheating, air is moved through the housing by the fan to cool the operation of the lamp and other internal components, which is then expelled from the housing through an outlet vent area, which is often covered by a grid to prevent access to internal components. A problem exists in that it is desirable for pulse repetition rate to be high which enables the device to be moved over the skin quickly improving ease of use. As a result there is reduced time in between each pulse for the device to cool. Therefore, significant amounts of heat can be generated, and the air can be at a high temperature which may exceed 80° C. As a result the housing temperature may increase to a value which is higher than regulatory safety limits that prevent burning of a user. This is clearly undesirable. One method of mitigating this is to reduce the firing rate. This reduction in firing rate may be continuous, or adaptive, based on a monitored temperature of a component of the device such as the housing and preventing firing of the lamp if the temperature of the housing exceeds a predetermined safe value. The effect of this however is an overall reduction in pulse repetition rate meaning operation is slower and the treatment takes longer. Furthermore, operation can be inconsistent if the device is being drawn across the skin at an approximately constant speed, then firing of the lamp may be at irregular intervals reducing efficacy of treatment as some areas of the skin will undergo different treatments to other areas.

The present invention provides an improved arrangement.

According to the present invention there is a light emitting apparatus for dermatological treatment comprising a housing structure for housing a light emitting source, a fan and a duct, the light emitting source arranged to emit light energy to external of the device, the fan configured for directing air heated by operation of the light emitting source into the duct, the duct being arranged to direct heated air in an airstream pathway from an outlet port of a distal end of the duct and through an aperture in the housing structure, wherein the housing structure and the duct are relatively arranged such that no part of the housing structure extends into the airstream pathway in order to minimise heat exchange from the heated air to the housing structure.

The light emitting apparatus is beneficially an Intense Pulsed Light (IPL) apparatus. The IPL apparatus is beneficially utilised for cosmetic hair removal.

The present invention enables an improved air flow of air heated by the light emitting source away from the apparatus thereby enabling the time between pulses of light energy being emitted by the light source (pulse repetition rate) to be decreased. This provides significant benefits in operation as the apparatus can be moved over the skin at a faster rate whilst still maintaining efficacy. The hold period where a user cannot move the apparatus due to the necessary cooling time between pulses can be eliminated.

The housing structure has the user accessible external surfaces of the device that can be easily touched during normal use.

The duct beneficially focusses the airstream out of the housing structure in a direction that is not towards the housing structure. However, it will be appreciated that depending on for example external conditions to the apparatus or speed of movement of the apparatus itself there may be some deflection of heated air exiting the duct towards the housing arrangement.

However, the present invention minimises this effect through the relative configuration of the duct and housing structure to provide no part of the housing structure in the focussed airstream pathway.

It will be appreciated that the housing structure provides a handset for a user to grasp.

The relative configuration of the duct outlet and housing structure is beneficially such that the hot air exits the handset in one or more high speed jets that minimise contact between the heated air and the surrounding housing structure thus minimising heat exchange from the hot air to the housing structure that is held by a user.

The housing aperture has a length and a width both in an axis substantially perpendicular to the airstream pathway, wherein the width is small enough that a finger cannot be readily inserted. A suitable width is less than about 6 mm. Thus the aperture of the housing is small enough that a finger cannot be readily inserted. The housing aperture is preferably elongate in an axis substantially perpendicular to the airstream pathway, the length of the aperture is preferably significantly greater than the width. This configuration prevents insertion of a finger whilst also ensures high air flow rate from the housing structure.

The duct and housing structure are beneficially relatively arranged to direct the airstream away from and substantially perpendicular to the housing structure. Thus, irrespective of the external shape of the housing structure (preferably convex) the airstream is directed away from the housing structure in a direction that minimises heating of the housing structure either side of the airstream and effectively centralises the airstream between either side of the housing structure defining the aperture.

The airstream is uninterrupted after exiting the distal end of the duct. It is beneficial that a grid or mesh or similar that can be easily touched by the user is not provided covering the outlet port. In the present invention the aperture in the housing structure may be kept open and uninterrupted by a grid or mesh, meaning there is no touchable grid or mesh provided directly in the airflow pathway becoming heated by the exhaust air jet and thus forming a burning hazard to a user.

It may be beneficial to use a material for the aperture surround area of the housing structure that has a low thermal conductivity such as thermoplastic.

The distal end of the duct is beneficially insulated from the housing structure. This beneficially reduces conduction of heat from the relatively hot duct to the handset enclosure. The distal end of the duct is preferably insulated from the housing by a separation gap, preferably an air gap. It is beneficial that the insulation is provided by a space defined between a portion of the distal end of the duct and the housing structure. It is preferable that the space extends around a majority of the distal end of the duct. The space may be an annular space defined between the distal end of the duct and the housing.

The duct is preferably positioned inside the housing structure. The duct may therefore terminate rearwardly of the housing aperture. Thus, the distal end of the duct may be substantially hidden behind the housing structure. By positioning the duct in the housing structure the chance of accidental contact with the duct significantly heated by the airstream is minimised. The duct preferably comprises a duct opening at the distal end thereof substantially aligned with the opening defined by the housing aperture.

The housing aperture preferably comprises a housing duct having an inlet and an outlet, and wherein the duct tapers outwardly in the direction of the airflow intermediate the inlet and the outlet. The housing duct through which the airstream exits therefore beneficially does now have a constant cross sectional area. Instead the cross sectional area may increase towards the external surface of the housing structure. This configuration reduces the heating effect upon the edge of the housing structure defining the housing structure aperture due to any divergence of the airstream after exiting the distal end of the duct.

Despite the arrangements so far described, the housing material directly surrounding the housing structure aperture may still increase in temperature more than desired. Therefore, a further preferred feature of the invention is for the housing structure to comprise one or more air inlet ports for enabling airflow into the housing structure. This allows relatively cool air from outside the housing structure to be drawn into the housing structure through the air inlet ports or cooling ducts due to the pressures generated by fan. The flow of air through the cooling ducts will act to cool the material surrounding the aperture thus helping to prevent an excessive temperature rise. The one or more air inlet ports may be located adjacent the housing aperture. The air inlet ports provide a secondary (or more) airflow path in addition to the main lamp cooling airflow that is designed for keeping the housing structure cool. A plurality of air inlet ports may be provided in array adjacent the housing aperture.

The fan is preferably a radial fan. A radial fan enables the housing to be have a reduced size in comparison to an axial fan due to relatively high pressure and flow rate that can be generated, and also the increased compactness of the air outlet.

The distal end of the duct is beneficially recessed relative to the housing structure. This provides a safety benefit in that it is more difficult for a user to touch the heated duct.

The cross-sectional area of the duct may reduce and may taper towards the distal end. This beneficially accelerates the flow of air improves smooth airflow through the duct creating a high speed jet.

The duct is at least partially curved. This aids in reducing the overall size of the housing structure, particularly when utilising a radial fan.

One or more baffles may be provided in the duct for reducing divergence and/or rotation of the airflow exiting the duct. These baffles, which may also be termed air flow guide ribs within the duct cannot be easily touched and may be used to help form and direct the high speed airstream.

Aspects of the present invention will now be described by way of example only with reference to the accompanying drawings where:

Figure 1:
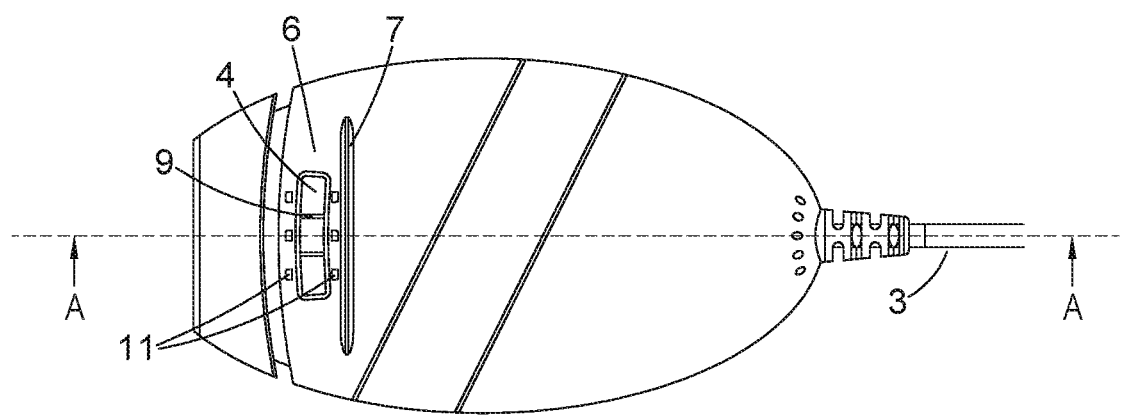
FIG. 1 is a plan view of an apparatus according to an exemplary embodiment of the present invention.
Figure 4:
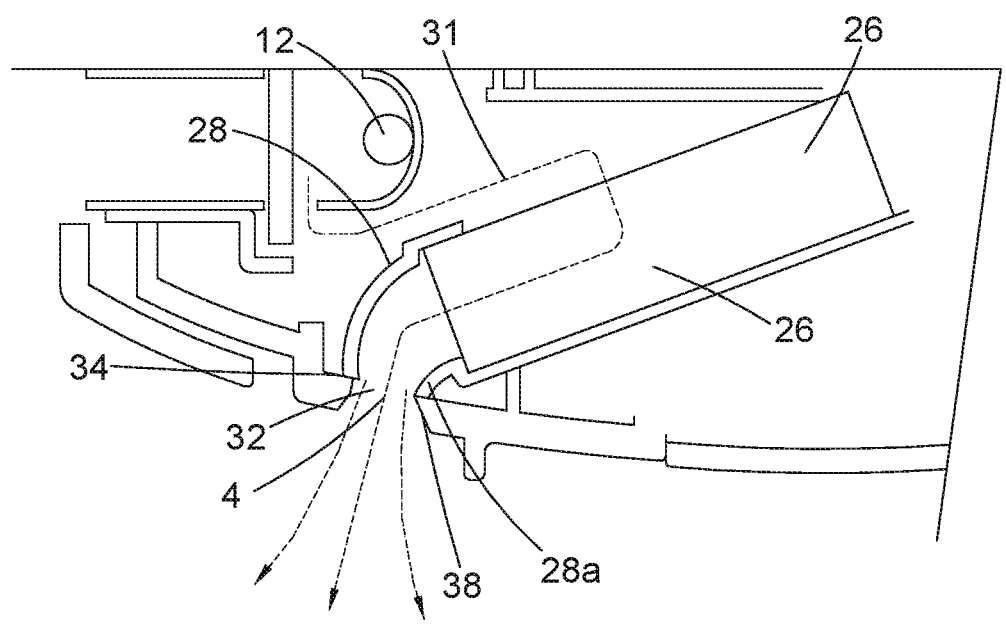
FIG. 4 is a schematic part cross sectional representation of an apparatus according to an alternative exemplary embodiment of the present invention.

Referring to FIG. 1 there is a schematic plan representation of an apparatus according to an exemplary embodiment of the present invention. The apparatus presented is an Intense Pulse Light (IPL) device comprising a housing structure in the form of a handset (6) connected via an umbilical cable (3) to a charging module (not shown). The charging module in turn is connected to a mains power supply). As described in more detail in subsequent figures there is a housing aperture (4) through which heated air is expelled. A dividing rib (7) may be provided for distinguishing to a user between the handle portion of the housing structure and the venting portion incorporating the aperture (4). As can be seen in FIG. 1, the aperture (4) is elongate having a length and a width, and the length is significantly greater than the width. Further as clearly shown in FIG. 4 are optional baffles (9) and air inlet ports (11) described in detail with respect to FIG. 4.

Figure 2:
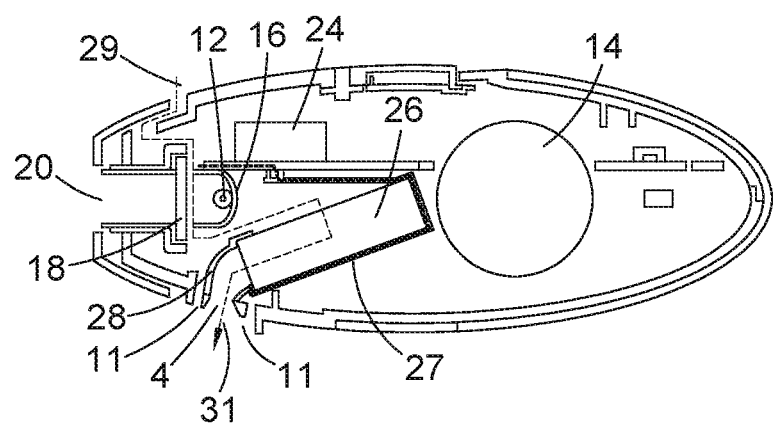
FIG. 2 is a schematic cross sectional view cut through line A-A of FIG. 1 according to an exemplary embodiment of the present invention.

Referring to FIG. 2 there is a cross-sectional representation through the handset (6) presenting the components of the handset. A flash lamp in the form of a xenon flash lamp (12) is provided and is driven by the storage capacitor (14). Light energy output from the lamp (12) is focused by reflector (16) forwardly through filter arrangement (18) which is present to remove harmful wavelengths of light below approximately 510 nm. The light energy having passed through the filter (18) is output from the apparatus from the mouth (20). One or more of a skin contact/skin tone sensor (not shown) is provided at the forward end of the handset (6) adjacent to the mouth (20). Such a skin contact/tone sensor (22) is in communication with the controller taking the form of a control PCB (24) to prevent operation of the apparatus unless a valid skin contact/tone reading is received.

Due to the significant amount of heat generated by the lamp (12) a cooling fan (26) is provided to draw air into the handset (6) thereby cooling the lamp. Hot air is output through the duct (28) and exits the handset from housing aperture (4). Further components comprise a user operable actuator in the form of a button to cause operation of the device and there is further provided a skin contact indicator light indicating that the forward end of the handset is in contact or is in proximity to the skin.

The duct (28) can be seen to provide an airflow pathway to directing an airstream from the fan (26) to the outlet aperture (4). The fan (26) is a radial fan. The duct (28) can be seen to have a maximum cross-sectional area adjacent the fan (26) reducing to a minimum cross-sectional area at the outlet aperture (4). The speed of the heated air travelling through the duct (28) may be increased towards the outlet aperture (4). The duct (28) itself may taper towards the outlet aperture (4).

The fan (26) itself may be retained by an enclosure (27) and in operation draws in heated air axially and expels the heated air radially into the duct (28). A primary airflow inlet (29) is beneficially provided to ensure sufficient air flow through the housing (6) and out through the aperture (4). Additional air inlet ports (11) can be seen adjacent to aperture (4). As presented in FIG. 2, dashed line (31) represents air flow pathway through the housing (6).

Figure 3:
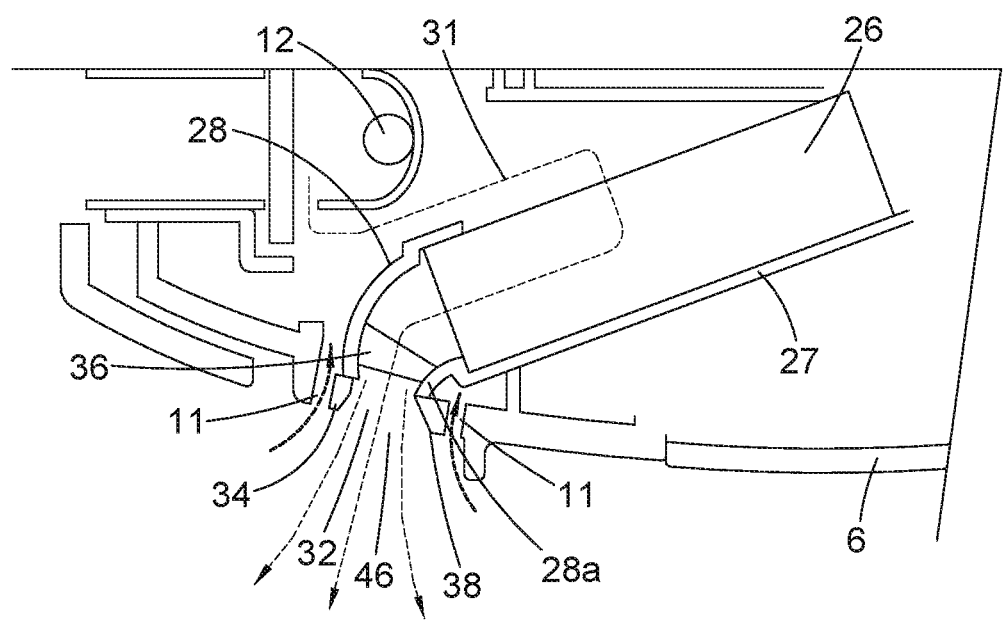
FIG. 3 is a magnified schematic representation of the air flowpath through the apparatus as presented in FIG. 2.

Referring now to FIG. 3 the fan (26), duct (28) and aperture (4) are presented in more detail. Duct (28) provides the function of directing heated air in an airstream pathway from the fan (26) to an outlet port (32) at the distal end of the duct (28a). The duct (28) directs the heated air in the airstream pathway through the aperture (4) provided in the housing (6). The duct (28) and housing (6) are relatively arranged such that no part of the housing structure extends into the airstream pathway exiting from the duct (28). This is clearly apparent in FIG. 3. Thus, the airstream is uninterrupted as it exits the outlet (32) of the distal end (28) of the duct. The distal end of the duct (28a) is positioned rearwardly of housing (6). It is thus extremely difficult for a user to accidently contact the distal end of the duct (28a) which will be hot due to the effect of the heated air passing therethrough. A small separation gap (34) is preferably provided between the distal end of the duct (28a) and the housing (6) to prevent conduction of heat therebetween. One or more baffles (36) may be provided in the duct (28) to improve alignment of the air flow in the air stream pathway. This further improves the coherence of the direction of travel of the air through the duct (28) and improves air coherence exiting the opening (28a) and thus the aperture (4).

To further reduce the effect of heating of the housing (6) the aperture (4) is defined by a wall (38) that tapers outwardly from an upstream to a downstream location and is thus wider at the outlet than the inlet. This further reduces heating of the housing (6) adjacent to the aperture (4) due to any dispersion of the heated airflow after existing the apparatus. Accordingly, heat exchange from the heated air to the housing structure is minimised.

Referring now to FIG. 4, an embodiment of the invention is presented in a cross section as presented in FIG. 3 without the provision of additional air inlet ports (11). Again a separation gap (34) is beneficial between the distal end (28a) of the duct and the housing (6). Furthermore, the optional baffles (36) have not been positioned in the duct (28). Importantly, however, no part of the housing (6) extends into the airstream pathway in order to minimise heat exchange from the heated air to the housing.

Additional changes or modifications may be forming the duct (28) integrally with the fan (26). It will also be appreciated that an axial fan could be utilised.

Aspects of the present invention have been described by way of example only and it will be appreciated to the skilled addressee that modifications and variations made be made without departing from the scope of protection afforded by the appended claims.

The invention claimed is:

1. A light emitting apparatus for dermatological treatment comprising:
   a housing structure for housing a light emitting source;
   a fan; and
   a duct;
   wherein the light emitting source is arranged to emit light energy to external of the apparatus;
   wherein the fan is configured for directing air heated by operation of the light emitting source into the duct;
   wherein the duct is arranged to direct heated air in an airstream pathway from an outlet port of a distal end of the duct and through a housing aperture being an aperture in the housing structure;
   wherein the distal end of the duct is insulated from the housing structure; and
   wherein the housing structure and the duct are relatively arranged such that no part of the housing structure extends into the airstream pathway in order to minimize heat exchange from the heated air to the housing structure.

2. The apparatus according to claim 1, wherein the housing aperture has a length and a width both in an axis substantially perpendicular to the airstream pathway; and
   wherein the width is small enough that a finger cannot be readily inserted.

3. The apparatus according to claim 1, wherein the housing aperture has a length and a width both in an axis substantially perpendicular to the airstream pathway; and
   wherein the width is less than about 6 mm.

4. The apparatus according to claim 1, wherein the housing aperture is elongate in an axis substantially perpendicular to the airstream pathway.

5. The apparatus according to claim 1, wherein the duct and housing structure are relatively arranged to direct the airstream pathway away from and substantially perpendicular to the housing structure.

6. The apparatus according to claim 1, wherein the insulation is provided by a space defined between a portion of the distal end of the duct and the housing structure.

7. The apparatus according to claim 6, wherein the space extends around a majority of the distal end of the duct.

8. The apparatus according to claim 6, wherein the space is an annular space defined between the distal end of the duct and the housing.

9. The apparatus according to claim 8, wherein the space comprises an air inlet to an air flow pathway to the fan.

10. The apparatus according to claim 1, wherein the distal end of the duct is recessed relative to the housing structure.

11. The apparatus according to claim 1, wherein the duct is positioned inside the housing structure.

12. The apparatus according to claim 11, wherein the duct comprises a duct opening at the distal end thereof substantially aligned with an opening defined by the housing aperture.

13. The apparatus according to claim 1, wherein the housing aperture comprises a housing duct having an inlet and an outlet; and
   wherein the duct tapers outwardly in the direction of an airflow intermediate the inlet and the outlet.

14. The apparatus according to claim 1, wherein the housing structure comprises an air inlet port enabling airflow into the housing.

15. The apparatus according to claim 14, wherein the air inlet port is located adjacent the housing aperture.

16. The apparatus according to 1, wherein the housing structure comprises a plurality of air inlet ports enabling airflow into the housing; and
   wherein the plurality of air inlet ports are provided in an array.

17. The apparatus according to claim 1, wherein the fan is a radial fan.

18. The apparatus according to claim 1, wherein the duct is at least partially curved.

19. The apparatus according to claim 1 further comprising a baffle provided in the duct for reducing one or both of divergence and rotation of an airflow exiting the duct.

20. The apparatus according to claim 1, wherein the duct has a length extending from the fan to the distal end; and
   wherein a cross-sectional area of the duct reduces towards the distal end.

21. The apparatus according to claim 20, wherein the cross-sectional area of the duct tapers towards the distal end.

22. A light emitting apparatus for dermatological treatment comprising:
- a housing structure for housing a light emitting source;
- a fan; and
- a duct;
- wherein the light emitting source is arranged to emit light energy to external of the apparatus;
- wherein the fan is configured for directing air heated by operation of the light emitting source into the duct;
- wherein the duct is arranged to direct heated air in an airstream pathway from an outlet port of a distal end of the duct and through a housing aperture being an aperture in the housing structure;
- wherein the distal end of the duct is insulated from the housing structure via a space defined between a portion of the distal end of the duct and the housing structure;
- wherein the space comprises an air inlet to an air flow pathway to the fan; and
- wherein the housing structure and the duct are relatively arranged such that no part of the housing structure extends into the airstream pathway in order to minimize heat exchange from the heated air to the housing structure.

\* \* \* \* \*